(12) United States Patent
Arnholt et al.

(10) Patent No.: US 10,492,939 B2
(45) Date of Patent: Dec. 3, 2019

(54) DEFLATION NEEDLE WITH STABILIZATION FEATURES AND RELATED METHODS

(71) Applicant: Boston Scientific Scimed, Inc., Maple Grove, MN (US)

(72) Inventors: Devon N. Arnholt, Shoreview, MN (US); Douglas D. Pagoria, Forest Lake, MN (US); Joel T. Eggert, Plymouth, MN (US); Todd College, Little Canada, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 521 days.

(21) Appl. No.: 14/603,885

(22) Filed: Jan. 23, 2015

(65) Prior Publication Data
US 2015/0209168 A1 Jul. 30, 2015

Related U.S. Application Data

(60) Provisional application No. 61/931,939, filed on Jan. 27, 2014.

(51) Int. Cl.
*A61F 5/00* (2006.01)

(52) U.S. Cl.
CPC ............ *A61F 5/003* (2013.01); *A61F 5/0036* (2013.01); *A61F 5/0089* (2013.01)

(58) Field of Classification Search
CPC ...... A61F 5/003; A61F 5/0089; A61F 5/0036; A61M 25/04; A61M 25/0017; A61M 25/00

(Continued)

(56) References Cited

U.S. PATENT DOCUMENTS 5,419,763 A * 5/1995 Hildebrand ........ A61M 25/1011
604/101.03
6,083,198 A * 7/2000 Afzal .................. A61M 25/007
604/101.01

(Continued)

FOREIGN PATENT DOCUMENTS

EP 0935977 A2 * 8/1999 ........ A61M 25/0017
EP 2 026 719 12/2007

*Primary Examiner* — George J Ulsh
(74) *Attorney, Agent, or Firm* — Seager, Tufte & Wickhem, LLP

(57) ABSTRACT

According to an aspect of the present disclosure, a medical device may include a deflation catheter assembly. The deflation catheter assembly may include a tubular member having an outer surface, an inner surface, and a central lumen defined by the inner surface. The deflation catheter assembly may also include a plurality of passages extending through a side of the tubular member and from the inner surface to the outer surface. The deflation catheter assembly may also include an anchoring member coupled to the tubular member. A distal portion of the tubular member may extend distal the anchoring member. The plurality of passages may be at the distal portion of the tubular member. The anchoring member may be configured to move between an unexpanded state and an expanded state. At least a portion of the anchoring member may protrude radially outwardly from the outer surface of the tubular member when the anchoring member is in the expanded state.

21 Claims, 7 Drawing Sheets

(58) Field of Classification Search
USPC .......................................................... 606/191
See application file for complete search history.

(56) References Cited

U.S. PATENT DOCUMENTS

| | | |
|---|---|---|
| 2007/0288033 A1 | 12/2007 | Murature et al. |
| 2010/0168783 A1 | 7/2010 | Murature et al. |
| 2011/0152741 A1* | 6/2011 | Banchieri ........... A61M 1/3653 604/6.16 |
| 2011/0208022 A1* | 8/2011 | Brawer .............. A61B 10/0045 600/309 |

* cited by examiner

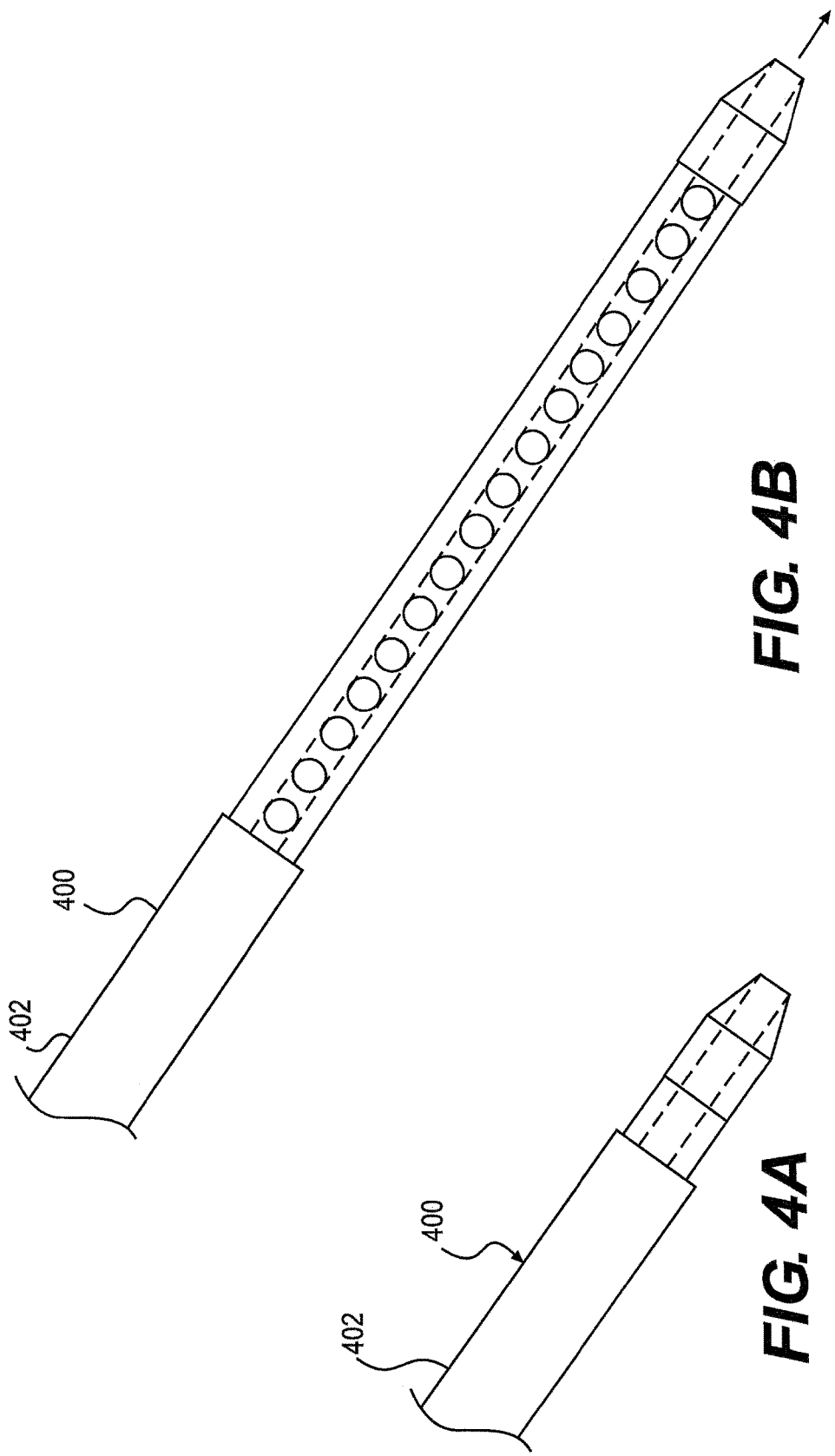

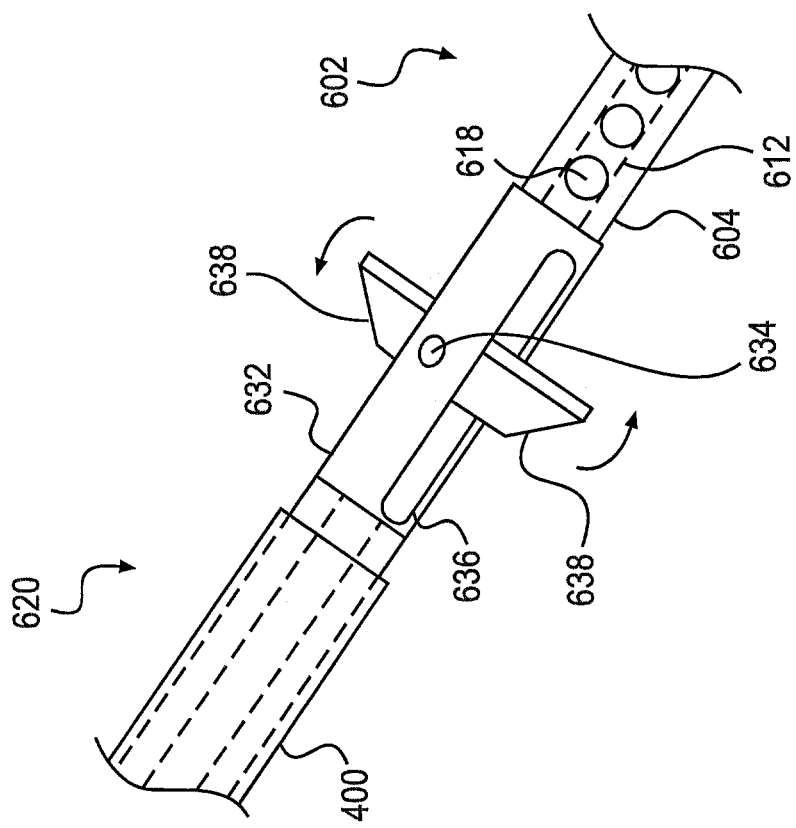
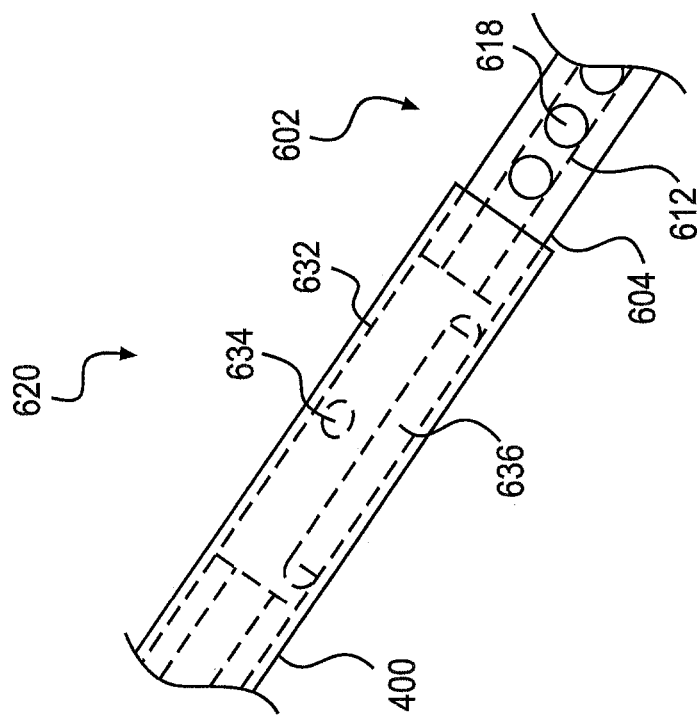
FIG. 6B
FIG. 6A

DEFLATION NEEDLE WITH STABILIZATION FEATURES AND RELATED METHODS

CROSS-REFERENCE TO RELATED APPLICATIONS

This application claims the benefit of priority from U.S. Provisional Application No. 61/931,939, filed on Jan. 27, 2014, which is incorporated by reference herein in its entirety.

FIELD OF THE DISCLOSURE

This disclosure relates generally to devices and methods for deflating inflatable devices. More particularly, the disclosure relates to deflation devices, and related methods, for deflating intragastric balloons and similar fluid filled devices.

BACKGROUND OF THE DISCLOSURE

Intragastric balloon surgery for treating obesity involves insertion and placement of an inflatable member, such as an intragastric balloon, in the stomach. The intragastric balloon, when inflated, may occupy a portion of the volume of the interior of a patient's stomach, thereby reducing feeling of hunger in the patient. The intragastric balloon may be inflated by filling an interior volume of the intragastric balloon with a fluid, such as a gas. After a period of time, the balloon may be deflated and removed from the stomach.

Deflating the intragastric balloon may be attempted using a deflation member with a distal opening in fluid communication with a lumen. The deflation member may be inserted through an opening in a wall of the inflated intragastric balloon. Fluid in the inflated intragastric balloon may be withdrawn from, or otherwise flow out of, the interior volume of the intragastric balloon, by passing through the distal opening and the lumen of the deflation member and travelling out of the intragastric balloon.

However, in some instances, deflation of the intragastric balloon may cause the intragastric balloon to deflate or collapse in ways that the intragastric balloon may take on irregular shapes. For example, the intragastric balloon may deflate in a way that one or more pockets of fluid may be present in the intragastric balloon, the pockets being formed, for example, by contacting portions of the wall of the intragastric balloon. Those or other portions of the balloon wall may obstruct the distal opening of the deflation member during deflation of the intragastric balloon. As a result, fluid may be blocked from flowing out of the intragastric balloon. Thus, the intragastric balloon may remain partially inflated. If the intragastric balloon is partially inflated, it may be more difficult to remove from the interior of the stomach due to its size.

In some other instances, the deflation member may move back and forth in the balloon to withdraw the fluid or gas. During this movement, a portion of the balloon may be emptied while some portions of the balloon may still be filled with the fluid or gas. It may be difficult to move the deflation member back and forth in all the directions of the balloon in order to withdraw 100% or substantially 100% of the fluid or gas from the balloon. Sometimes, excessive back and forth movement may cause a sudden unintentional withdrawal of the deflation member from an opening of the balloon. It may be difficult to repuncture the balloon and reinsert the deflation member in the balloon. For example, the inflated balloon may have a harder outer surface and therefore be easier to puncture, as compared to the softer outer surface of the partially deflated balloon.

Thus, it may be beneficial to provide apparatus as well as methods of use thereof that address or overcome some or all of the above issues.

SUMMARY OF THE DISCLOSURE

The present disclosure describes a medical device for deflating an inflated intragastric balloon in the stomach of the patient.

According to an aspect of the present disclosure, a medical device may include a deflation catheter assembly. The deflation catheter assembly may include a tubular member having an outer surface, an inner surface, and a central lumen defined by the inner surface. The deflation catheter assembly may also include a plurality of passages extending through a side of the tubular member and from the inner surface to the outer surface. The deflation catheter assembly may also include an anchoring member coupled to the tubular member. A distal portion of the tubular member may extend distal the anchoring member. The plurality of passages may be at the distal portion of the tubular member. The anchoring member may be configured to move between an unexpanded state and an expanded state. At least a portion of the anchoring member may protrude radially outwardly from the outer surface of the tubular member when the anchoring member is in the expanded state.

According to another aspect of the present disclosure, a medical device for deflating an inflated intragastric balloon, by allowing a fluid in the intragastric balloon to exit from an interior of the intragastric balloon, may include a deflation catheter assembly. The deflation catheter assembly may include a tubular member having an outer surface, an inner surface, and a central lumen defined by the inner surface. The deflation catheter may also include a plurality of passages extending through a side of the tubular member from the inner surface to the outer surface. The plurality of passages may be configured to allow the fluid to flow from the interior of the intragastric balloon, into the plurality of passages, and into the central lumen of the tubular member. The deflation catheter assembly may also include an anchoring member coupled to the tubular member. A distal portion of the tubular member may extend distal the anchoring member. The passages may be at the distal portion of the tubular member. The anchoring member may be configured to move between an unexpanded state and an expanded state. In the expanded state, at least a proximal portion of the anchoring member may extend radially outwardly from the outer surface of the tubular member, for engaging an inner surface of the intragastric balloon.

According to an aspect of the present disclosure, a method for deflating an inflated intragastric balloon, the inflated intragastric balloon including a wall surrounding an interior chamber containing a fluid, may include inserting a tubular member of a deflation catheter assembly through an opening in the wall of the inflated intragastric balloon. The method may also include positioning a plurality of passages extending through a side of the tubular member within the interior chamber of the inflated intragastric balloon. The method may also include expanding an anchoring member mounted on the tubular member. The anchoring member may be proximal the plurality of passages. The expanded anchoring member may be wider than the opening in the wall of the inflated intragastric balloon. The method may also include withdrawing the fluid by allowing the fluid to flow from the interior chamber, into the plurality of passages, and into a central lumen of the tubular member.

Additional aspects and advantages of the described embodiments will be set forth in part in the description that follows, and in part will be apparent from the description, or, may be learned by practicing the disclosure. The aspects and/or advantages of the disclosure will be realized and attained by way of the elements and combinations particularly pointed out in the appended claims.

It is to be understood that both the foregoing general description and the following detailed description are exemplary and explanatory only, and are not restrictive of the described embodiments, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 4A and 4B are schematic top views of another deflation catheter assembly, according to aspects of the present disclosure;

FIGS. 6A and 6B are schematic top views of another deflation catheter assembly, according to aspects of the present disclosure.

DESCRIPTION OF THE EMBODIMENTS

Reference will now be made to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. The term "proximal" refers to the end closest to the medical professional when placing a device in the patient.

Overview

Embodiments of the present disclosure relate to devices and related methods for deflating inflatable members. For example, embodiments of the present disclosure may facilitate deflation of an intragastric balloon in a stomach of a patient.

Embodiments of the present disclosure may include a deflation catheter assembly. The deflation catheter assembly may include a tubular member having a central lumen in fluid communication with a distal end opening, and a plurality of side passages. The central lumen, distal end opening, and side passages may form a flow path through which fluid may exit from an interior of an inflated intragastric balloon. The deflation catheter assembly may also include an anchoring member to impede or prevent the tubular member from being prematurely withdrawn from the intragastric balloon.

Embodiments of the present disclosure may be used with an elongate device, including an endoscopic system for introducing and delivering medical devices to target sites within body of a patient. For example, embodiments of the present disclosure may be inserted through lumens of sheaths, trocars, cannulae, catheters, endoscopes, laparoscopes, colonoscopes, ureteroscopes, or the like.

Exemplary Embodiments

Figure 1:
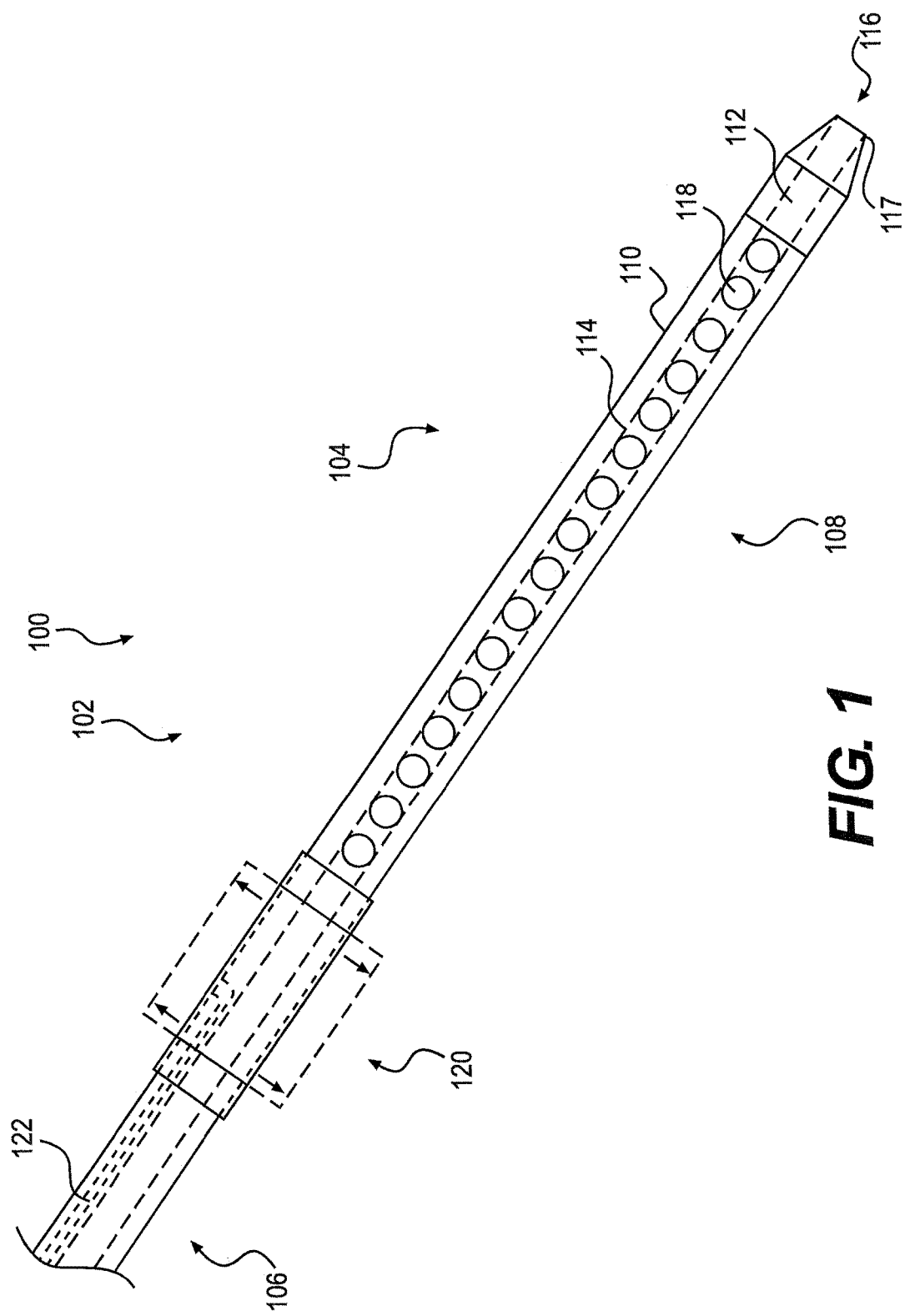
FIG. 1 is a schematic top view of a deflation catheter assembly, according to aspects of the present disclosure.

FIG. 1 is a schematic top view of a medical device 100 including a deflation catheter assembly 102. The deflation catheter assembly 102 may include a tubular member 104 having a proximal portion 106 and a distal portion 108. The tubular member 104 may be an elongated member configured to reach a target area. The target area may include, for example, a patient's stomach. The tubular member 104 may be substantially cylindrical, having a substantially circular cross-section. In other embodiments, the tubular member 104 may have a cross-section in the shape of a triangle, square, oval, rectangle, and/or any other suitable shape. The tubular member 104 may be rigid, or semi-rigid (e.g., sufficiently flexible to be navigated to the target site through a passage, but rigid enough to penetrate a wall of an intragastric balloon). The tubular member 104 may be formed from plastic, nitinol, stainless steel or other metals, biocompatible materials, and/or combinations thereof. In some embodiments, the tubular member 104 may be coated with a lubricious material, such as Teflon or the like, for ease of insertion.

The tubular member 104 may include an outer surface 110, an inner surface 114, and a central lumen 112 defined by the inner surface 114. The central lumen 112 may have dimensions sufficient to allow a fluid or a gas to flow therein. The central lumen 112 may have a substantially circular cross-section. It is also contemplated, however, that the central lumen 112 may have any other suitable cross-sectional shape.

A plurality of passages 118 may be disposed on the distal portion 108, and may extend through a side of the tubular member 104 from the inner surface 114 to the outer surface 110. The passages 118 may be in fluid communication with the central lumen 112. Fluid may flow through each of the passages 118 and into the central lumen 112. The passages 118 may have a substantially circular cross-section, or any other suitable shape.

The passages 118 may be arranged linearly along one side surface of the tubular member 104. In another embodiment, the passages 118 may be arranged along multiple side surfaces of the tubular member 104, and/or circumferentially around the tubular member 104. The size, shape, and positioning of the passages 118 may be selected to facilitate fluid flow, while maintaining structural integrity of the tubular member 104.

The tubular member 104 may have a distal opening 116 at a distal end 117 of the distal portion 108. The distal opening 116 may have dimensions sufficient to allow the fluid to pass therethrough, and to allow medical devices, such as needles, to pass therethrough. The distal opening 116 may be in fluid communication with the central lumen 112. The distal portion 108 may be tapered approaching the distal end 117. The reduced dimensions of the distal end 117 facilitate its insertion through openings and passages. The distal opening 116 may be substantially circular, but it should be understood that any other suitable shapes may be used. Alternatively, the distal portion 108 may taper into a pointed end (not shown) without a distal opening 116. The pointed end may be used for puncturing.

An anchoring member 120 may be coupled to the tubular member 104, such that the distal portion 108 extends distal to the anchoring member 120. The anchoring member 120 may encompass a substantial portion of the tubular member 104. The anchoring member 120 may be fixedly or permanently coupled to the tubular member 104. Alternatively, the anchoring member 120 may be removably coupled to the tubular member 104. The anchoring member 120 may be formed from a flexible and/or elastic material, including, for example, silicone, rubber, or any other suitable materials.

The anchoring member 120 may be configured to move between an unexpanded (deflated) state and an expanded (inflated) state. In the unexpanded state, portions of the anchoring member 120 may lie adjacent the outer surface 110 of the tubular member 104, such that the anchoring member 120 is nearly flush with the outer surface 110. In the expanded state, those portions of the anchoring member 120 may extend radially outwardly from the outer surface 110 of the tubular member 104 (the expanded state being shown in dashed lines in FIG. 1).

The tubular member 104 may include a peripheral lumen 122 in fluid communication with an interior volume of the anchoring member 120. A fluid may be directed through the peripheral lumen 122 and into the anchoring member 120, to inflate or expand the anchoring member. The anchoring member 120 may be deflated to its unexpanded state by removing the fluid via the peripheral lumen 122. The peripheral lumen 122 may have any size and cross-sectional shape suitable for performing the inflation and deflation functions.

Figure 2:
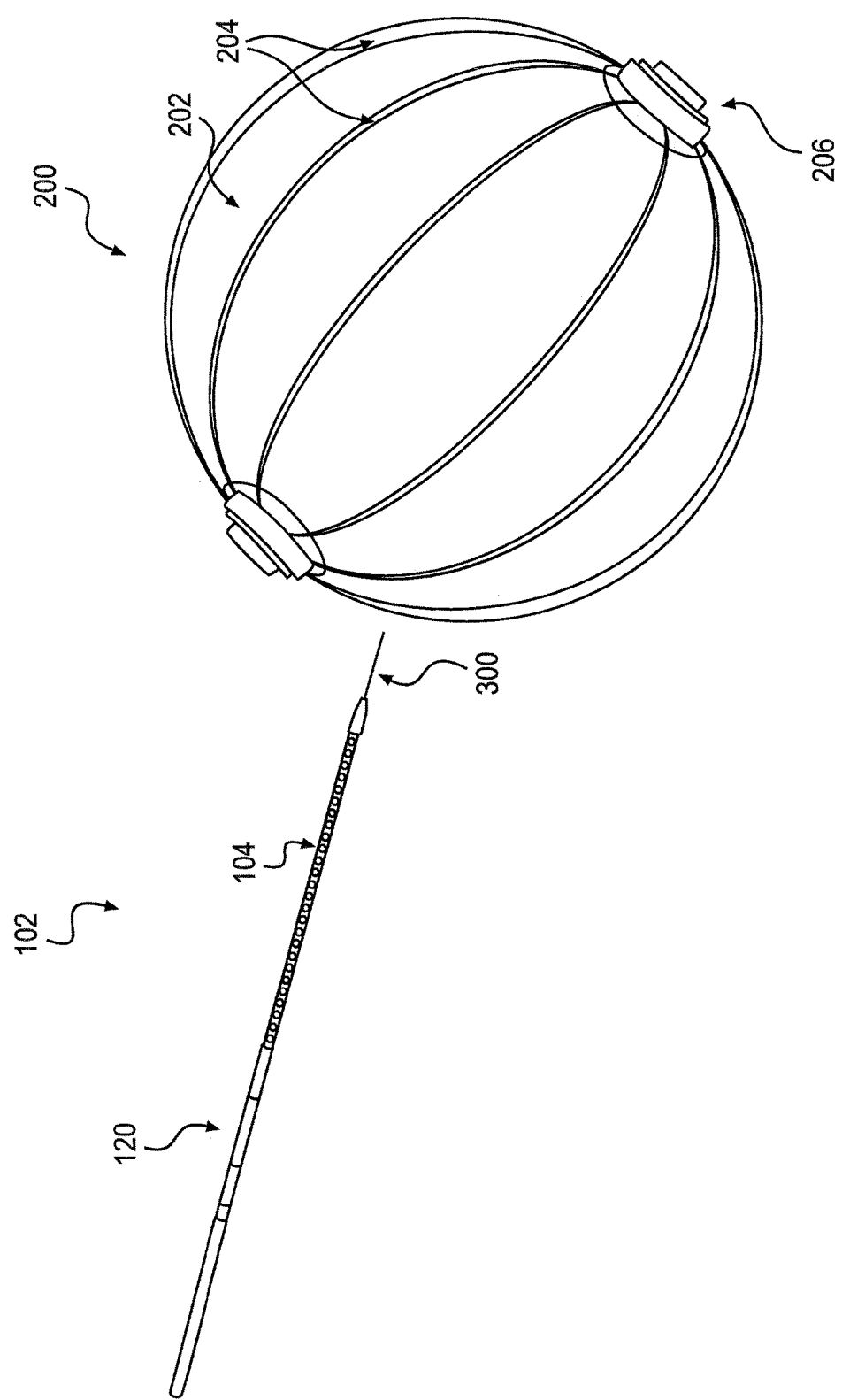
FIG. 2 illustrates the deflation catheter assembly of FIG. 1 advancing towards an intragastric balloon, according to aspects of the present disclosure.

FIG. 2 is a schematic top view of the deflation catheter assembly 102 advancing towards an intragastric balloon 200. The intragastric balloon 200 may be inserted and placed into the stomach of the patient, and inflated with a fluid, to occupy a portion of the interior volume of the stomach. The intragastric balloon 200 may be deflated to make it easier to insert and withdraw the intragastric balloon 200 from the stomach.

The intragastric balloon 200 may include supporting members, such as struts 204 and end caps 206, for supporting a wall 202. The wall 202 may include a continuous membrane extending around all of the struts 204, or a plurality of panels between adjacent struts 204. The wall 202 may be formed from any suitable flexible and/or elastic biocompatible material, such as silicone, rubber, and/or any other suitable elastomer. The struts 204 and end caps 206 may be made of any suitable material capable of supporting the wall 202, including biocompatible plastics, metals, alloys, and/or combinations thereof.

Figure 3:
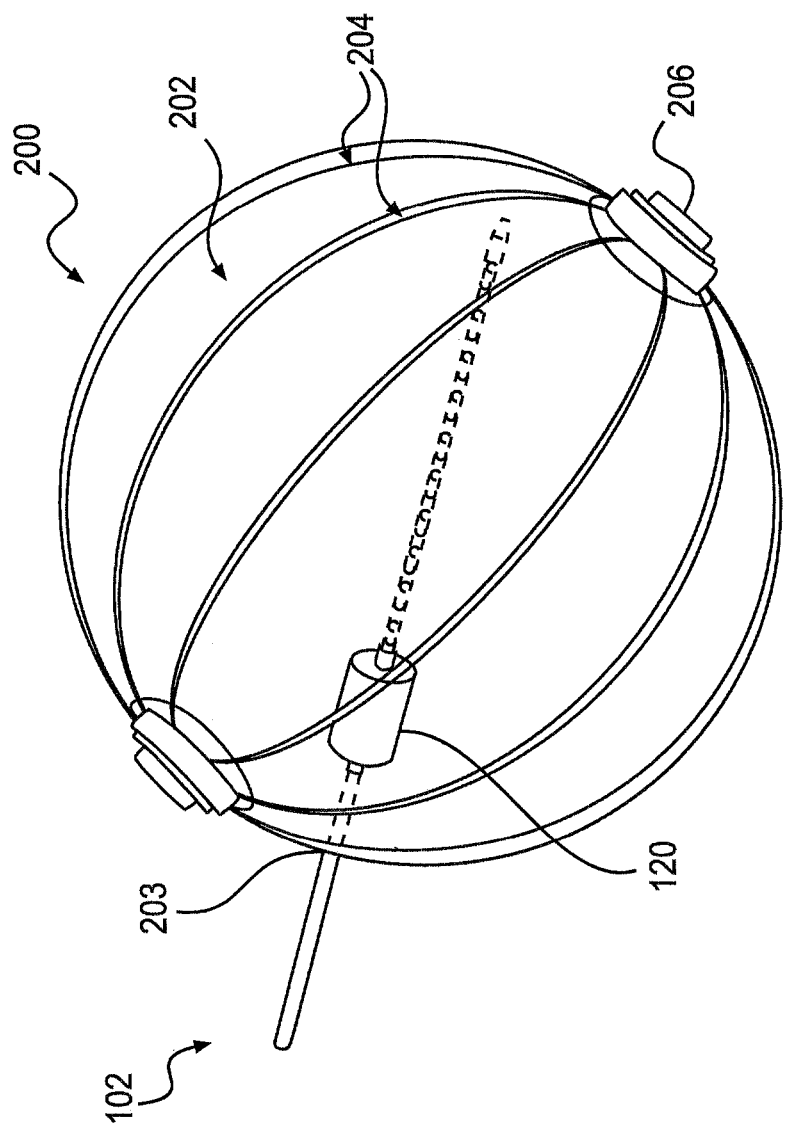
FIG. 3 illustrates the deflation catheter assembly of FIG. 1 after having penetrated the intragastric balloon, according to aspects of the present disclosure.

As shown in FIG. 2, a needle 300, or any other suitable puncturing member, may be inserted through the central lumen 112 of the tubular member 104, and may exit from the distal opening 116. The needle may puncture the wall 202 of the inflated intragastric balloon 200, thereby creating an opening 203 through the wall 202, shown in FIG. 3. The deflation catheter assembly 102 may be partially inserted through the opening 203 into the interior volume of the intragastric balloon 200. The needle 300 may be withdrawn from the deflation catheter assembly 102 in a proximal direction through the central lumen 112. The deflation catheter assembly 102 may be positioned such that the distal portion 108 and the anchoring member 120 of the deflation catheter assembly 102 may be within the interior volume of the inflated intragastric balloon 200. During insertion of the anchoring member 120 through the opening 203, the anchoring member 120 may remain in its deflated/unexpanded state.

Fluid or gas may be directed into the anchoring member 120 through the peripheral lumen 122 of the tubular member 104, to inflate/expand the anchoring member 120. When inflated, the anchoring member 120 may have a larger width than the width of the opening 203. As such, the expanded anchoring member may impede or prevent premature withdrawal of the deflation catheter assembly 102 from the intragastric balloon 200 during deflation, by abutting portions of the wall 202 surrounding the opening 203.

The deflation catheter assembly 102 may be moved around in the inflated intragastric balloon 200 to facilitate withdrawal of the fluid in the inflated intragastric balloon 200. The fluid may be travel into the distal opening 116 and/or the passages 118 of the tubular member 104, into the central lumen 112, and out of the interior of the intragastric balloon 200. If, during deflation, portions of the wall 202 obstruct or cover any of the distal opening 116 and the passages 118, those that remain unobstructed will continue to facilitate withdrawal of the fluid from the interior volume of the intragastric balloon 200. The inflated anchoring member 120 may also hold portions of the wall 202 that are proximal to the anchoring member 120, off of the distal portion 108, to reduce the likelihood of the passages 118 being obstructed or covered.

After the intragastric balloon 200 has been deflated, the anchoring member 120 may be deflated via the peripheral lumen 122, and the deflation catheter assembly 102 may be withdrawn from the deflated intragastric balloon 200. The deflated intragastric balloon 200 may be removed from the stomach by any suitable retrieval device. Additionally or alternatively, the anchoring member 120 may remain inflated, and may be used to engage the wall 202 of the deflated intragastric balloon 200, so that the deflation catheter assembly 102 may be used to help maneuver and/or withdraw the deflated intragastric balloon 200 from the stomach.

FIGS. 4A and 4B are schematic top views of a deflation catheter assembly retracted into (FIG. 4A), and extended out of (FIG. 4B), a sheath 400. The sheath 400 may extend from outside the patient to the target area, and may include an outer surface 402, and an inner surface 404 defining a central lumen 406 (FIG. 5). The central lumen 406 may be configured to receive the deflation catheter assembly. The sheath 400 and the deflation catheter assembly may be moved relative to each other to extend and retract the deflation catheter assembly from the sheath 400.

The sheath 400 and the central lumen 406 may have a circular cross-sectional shape, or any other suitable cross-sectional shape. The sheath 400 may be an endoscope, bronchoscope, laryngoscope, or the like. In some embodiments, an imaging device, such as a camera, may be attached at a distal portion of the sheath 400. The mini-camera may enable viewing of internal organs of the body of the patient to be viewed in order to assist the practitioner in locating the target area, and positioning the deflation catheter assembly.

Figure 5B:
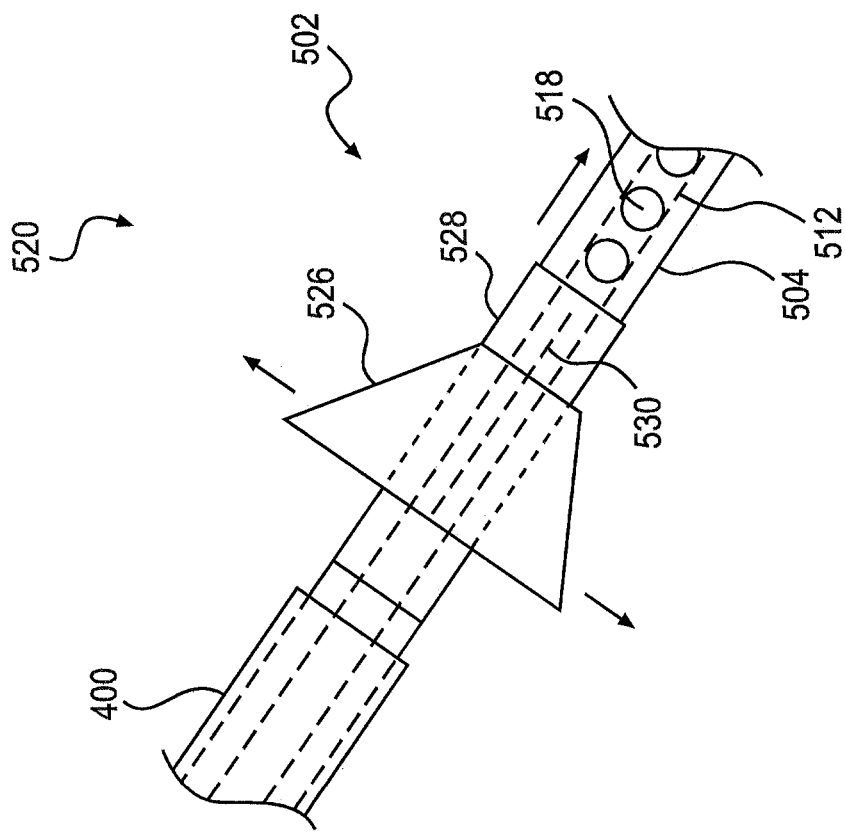
FIGS. 5A and 5B are schematic top views of another deflation catheter assembly, according to aspects of the present disclosure.
Figure 5A:
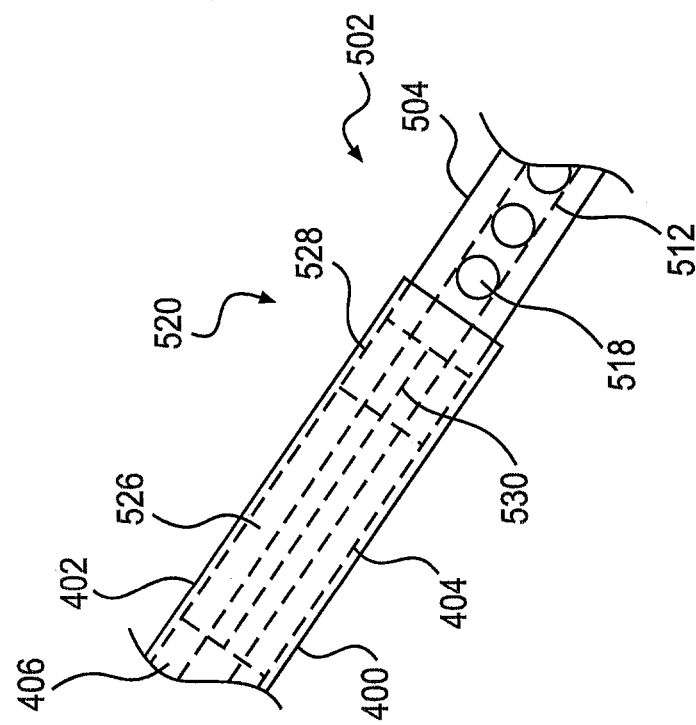

FIGS. 5A and 5B are schematic top views of an embodiment of a deflation catheter assembly 502, including a tubular member 504, a central lumen 512, and passages 518. The tubular member 504, central lumen 512, and passages 518, may be similar to the tubular member 104, central lumen 112, and passages 118 of the catheter assembly 102.

The deflation catheter assembly 502 may also include an anchoring member 520. The anchoring member 520 may be self-expandable. The anchoring member 520 may include a support 528, struts 530, and a canopy 526. The support 528 may wrap around and fixedly attach to the tubular member 504. When the anchoring member 520 is within the lumen 406 of the sheath, the interior surface of 404 of the sheath 400 may hold the anchoring member 520 in a collapsed/unexpanded state. When the anchoring member 520 is removed from within the sheath 400, the anchoring member 520 may move to its expanded state. Expansion of the anchoring member 520 may be driven by biasing forces generated by the struts 530. When expanded, the anchoring member 520 may have a conical shape (FIG. 5B). However, it is also contemplated that the struts 530 and the canopy 526 may expand to form other shapes, such as a cylindrical shape. For example, it is contemplated that the anchoring member 520 may expand into a cylinder similar to the shape of the inflated anchoring member 520. The struts 530 may also be replaced or assisted by a self-expandable stent (not shown), for supporting the canopy 526. Alternatively, the anchoring member 520 may expand to have a rectangular, triangular, or any other suitable cross-sectional shape. The width of the expanded anchoring member 520 may be larger than that of the opening 203 in the intragastric balloon 200, to restrict movement of the deflation catheter assembly 502 relative to the wall 202 of the intragastric balloon 200.

The support 128 and the struts 130 may be formed from any suitable material with sufficient strength to support the canopy 126, including but not limited to, plastic, nitinol, stainless steel, gold, silver, platinum, titanium, or the like, and/or combinations thereof. The canopy 126 may be formed from any flexible and/or elastic material, such as silicone, rubber, or other suitable elastomers.

FIGS. 6A and 6B are schematic top views of an embodiment of a deflation catheter assembly 602, including a tubular member 604, a central lumen 612, and passages 618. The tubular member 604, central lumen 612, and passages 618, may be similar to the tubular member 104, central lumen 112, and passages 118 of the catheter assembly 102.

The deflation catheter assembly 602 may also include an anchoring member 620. The anchoring member 520 include a housing 632, a pin 634 coupled to the housing 632, and a pivoting member 638 configured to rotate about the pin 634, relative to the housing 632. The housing 632 may include a slot 636. The pivoting member 638 may rotate between a retracted/unexpanded position (FIG. 6A) and an extended/expanded position (FIG. 6B). In the retracted position, the pivoting member 638 may be contained within the slot 636, and may be aligned with a longitudinal axis of the deflation catheter assembly 602. In the extended position, the pivoting member 638 may protrude from the slot 636, and may lie substantially perpendicular to the longitudinal axis of the deflation catheter assembly 602. The pivoting member 638 may be spring-biased to the extended position. For example, a spring (not shown) may be coupled to the pin 634 and the pivoting member 638, to bias the pivoting member 638 to the extended position. The sheath 400 may hold the pivoting member 638 in its retracted position until the anchoring member 620 is extended out of the sheath 400. The width of the pivoting member 638 may be larger than that of the opening 203 in the intragastric balloon 200, to restrict movement of the deflation catheter assembly 602 relative to the wall 202 of the intragastric balloon 200.

The housing 632 may connect portions of the tubular member 604. The slot 636 may be fluidly coupled to the central lumen 612 of the tubular member 604 by openings (not shown) in proximal and distal surfaces of the slot 636. Accordingly, the slot 636, in addition to receiving the pivoting member 638, may also act as passages for fluid flow, similar to the passages 618.

Figure 7B:
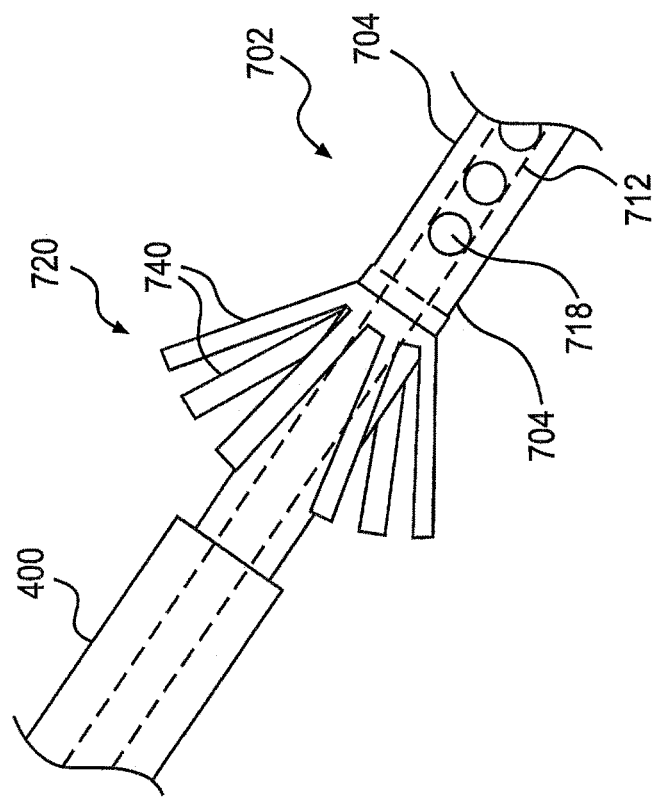
FIGS. 7A and 7B are schematic top views of another deflation catheter assembly, according to aspects of the present disclosure.
Figure 7A:
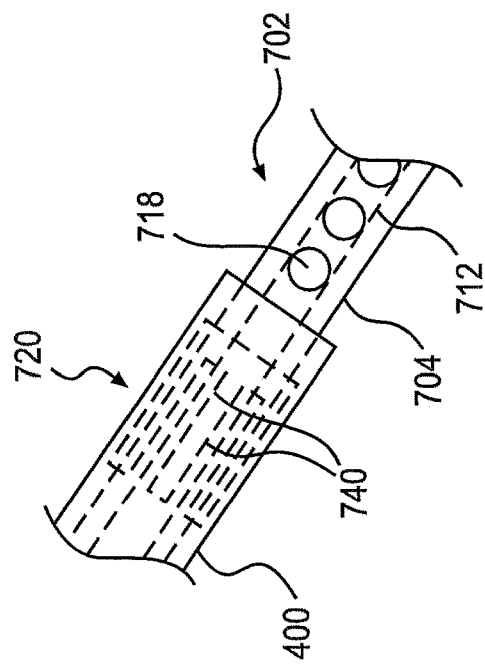

FIGS. 7A and 7B are schematic top views of an embodiment of a deflation catheter assembly 702, including a tubular member 704, a central lumen 712, and passages 718. The tubular member 704, central lumen 712, and passages 718, may be similar to the tubular member 104, central lumen 112, and passages 118 of the catheter assembly 102.

The deflation catheter assembly 702 may also include an anchoring member 720. The anchoring member 720 may be self-expandable. The anchoring member 720 may include a plurality of spring-biased prongs 740. When the anchoring member 720 is within the lumen 406 of the sheath, the interior surface of 404 of the sheath 400 may hold the anchoring member 720 in a collapsed/unexpanded state, with the prongs adjacent an outer surface of the tubular member 704. When the anchoring member 720 is removed from within the sheath 400, the anchoring member 720 may move to its expanded state. Expansion of the anchoring member 720 may be driven by biasing forces inherent in the prongs 740. When expanded, the prongs 740 may expand radially outward. The width of the expanded anchoring member 720 may be larger than that of the opening 203 in the intragastric balloon 200, to restrict movement of the deflation catheter assembly 702 relative to the wall 202 of the intragastric balloon 200. The anchoring member 720 may be made of any suitable material, including but not limited to, plastic, nitinol, stainless steel, gold, silver, platinum, titanium, or the like, and/or combinations thereof.

An exemplary method for using a sheath, similar to the sheath 400, and a deflation catheter assembly, similar to deflation catheter assemblies 502, 602, and 702, to deflate an inflated intragastric balloon 200, will now be described. The deflation catheter assembly may include a tubular member similar to the tubular members 504, 604, and 704; a central lumen similar to the central lumens 512, 612, and 712; and passages similar to the passages 518, 618, and 718. The deflation catheter assembly may also include an anchoring member, similar to the anchoring member 520, 620, and 720.

A needle 300 may be inserted through the central lumen of the tubular member, and may exit from a distal opening of the tubular member. The needle 300 may puncture the wall 202 of the inflated intragastric balloon 200, thereby creating an opening 203 through the wall 202, shown in FIG. 3. Alternatively, a distal end of the tubular member may not include the distal opening, but rather, may include a pointed tip. The pointed tip may puncture the wall 202. The pointed tip may be particularly useful if a needle 300 is prevented from extending through the central lumen by, for example, an anchoring member like the anchoring member 620.

The deflation catheter assembly may be partially inserted through the opening 203 into the interior volume of the intragastric balloon 200. The needle 300 may be withdrawn from the deflation catheter assembly in a proximal direction through the central lumen. The deflation catheter assembly may be inserted into the interior volume of the inflated intragastric balloon 200, until the anchoring member passes through the opening 203 and into the interior volume of the intragastric balloon 200. During insertion of the anchoring member through the opening 203, the anchoring member may remain in its unexpanded/retracted state. The anchoring member may be kept in its unexpanded/retracted state by the sheath 400. The sheath 400 may be inserted through the opening 203 with the deflation catheter assembly, or into contact with an outer surface of the wall 202 around the opening 230. The anchoring member may be extended out of the sheath 400 so that it expands/extends in the interior volume of the intragastric balloon 200.

When expanded/extended, the anchoring member may have a larger width than the width of the opening 203. As such, the expanded anchoring member may impede or prevent premature withdrawal of the deflation catheter assembly from the intragastric balloon 200 during deflation, by abutting portions of the wall 202 surrounding the opening 203.

The deflation catheter assembly may be moved around in the inflated intragastric balloon 200 to facilitate withdrawal of the fluid in the inflated intragastric balloon 200. The fluid may travel into the one or more openings (e.g., a distal opening, the side passages, and/or a slot like the slot 636) of the tubular member, into the central lumen, and out of the interior of the intragastric balloon 200. If, during deflation, portions of the wall 202 obstruct or cover any of the openings, those that remain unobstructed will continue to facilitate withdrawal of the fluid from the interior volume of the intragastric balloon 200. The expanded/extended anchoring member may also hold portions of the wall 202 that are proximal to the anchoring member, off of the distal portion of the tubular member, to reduce the likelihood of the passages being obstructed or covered.

After the intragastric balloon 200 has been deflated, the deflated intragastric balloon 200 may be removed from the stomach by any suitable retrieval device. Additionally or alternatively, the anchoring member may remain inflated, and may be used to engage the wall 202 of the deflated intragastric balloon 200, so that the deflation catheter assembly may be used to help maneuver and/or withdraw the deflated intragastric balloon 200 from the stomach.

Embodiments of the present disclosure may be used in any medical or non-medical environment. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device, comprising:
    a deflation catheter assembly, including:
        a tubular member having a distal tip with a distal opening, an outer surface, an inner surface, and a central lumen defined by the inner surface,
        three or more side passages extending through a side of the tubular member and from the inner surface to the outer surface,
        an anchoring member coupled to the tubular member, wherein:
            a distal portion of the tubular member extends distal the anchoring member to the distal tip,
            the three or more side passages are disposed in the distal portion of the tubular member between the distal tip and the anchoring member, and
            the anchoring member is configured to move between an unexpanded state and an expanded state, wherein at least a portion of the anchoring member protrudes radially outwardly from the outer surface of the tubular member when the anchoring member is in the expanded state, and
        a needle insertable through the central lumen of the tubular member.

2. The medical device of claim 1, wherein the anchoring member includes a balloon extending at least partially around a circumference of the tubular member.

3. The medical device of claim 2, wherein the tubular member includes a peripheral lumen in fluid communication with the balloon, for inflating the balloon.

4. The medical device of claim 1, wherein the anchoring member is biased to the expanded state.

5. The medical device of claim 4, further including a sheath having an outer surface, an inner surface, and a central lumen defined by the inner surface, the central lumen being configured to receive the tubular member and the anchoring member.

6. The medical device of claim 5, wherein the sheath is configured to move relative to the tubular member between a first position, wherein the inner surface of the sheath engages the anchoring member and keeps the anchoring member in the unexpanded state, and a second position, wherein the inner surface of the sheath is disengaged from the anchoring member, allowing the anchoring member to move to the expanded state.

7. The medical device of claim 4, wherein the anchoring member includes a self-expandable stent.

8. The medical device of claim 4, wherein the anchoring member has a conical shape when in the expanded state.

9. The medical device of claim 4, wherein the anchoring member includes a pivoting bar.

10. The medical device of claim 4, wherein the anchoring member includes a plurality of prongs.

11. A medical device for deflating an inflated intragastric balloon by allowing a fluid in the intragastric balloon to exit from an interior of the intragastric balloon, the medical device comprising:
    a deflation catheter assembly, including:
        a tubular member having a distal tip with a distal opening, an outer surface, an inner surface, and a central lumen defined by the inner surface, the distal tip being tapered and pointed,
        three or more side passages extending through a side of the tubular member from the inner surface to the outer surface, the three or more side passages being configured to allow the fluid to flow from the interior of the intragastric balloon, into the three or more side passages, and into the central lumen of the tubular member,
        an anchoring member coupled to the tubular member, wherein:
            a distal portion of the tubular member extends distal the anchoring member to the distal tip,
            the three or more side passages are disposed in the distal portion of the tubular member between the distal tip and the anchoring member, and
            the anchoring member is configured to move between an unexpanded state and expanded state, wherein in the expanded state at least a proximal portion of the anchoring member extends radially outwardly from the outer surface of the tubular member, for engaging an inner surface of the intragastric balloon, and
        a needle insertable through the central lumen of the tubular member.

12. The medical device of claim 11, wherein the anchoring member includes a balloon extending at least partially around a circumference of the tubular member.

13. The medical device of claim 12, wherein the tubular member includes a peripheral lumen in fluid communication with the balloon, for inflating the balloon.

14. The medical device of claim 11, wherein the anchoring member is biased to the expanded state.

15. The medical device of claim 14, further including a sheath having an outer surface, an inner surface, and a central lumen defined by the inner surface, the central lumen being configured to receive the tubular member and the anchoring member.

16. The medical device of claim 15, wherein the sheath is configured to move relative to the tubular member between a first position, wherein the inner surface of the sheath engages the anchoring member and keeps the anchoring member in the unexpanded state, and a second position, wherein the inner surface of the sheath is disengaged from the anchoring member, allowing the anchoring member to move to the expanded state.

17. The medical device of claim 14, wherein the anchoring member includes a self-expanding stent.

18. The medical device of claim 14, wherein the anchoring member has a conical shape in the expanded state.

19. The medical device of claim 14, wherein the anchoring member includes one of a pivoting bar and a plurality of prongs.

20. A method for deflating an inflated intragastric balloon, the inflated intragastric balloon including a wall surround an interior chamber containing a fluid, the method comprising:
　puncturing a wall of the inflated intragastric balloon with a needle exiting a distal opening of a central lumen of a tubular member of a deflation catheter assembly to create an opening;
　inserting the tubular member through the opening in the wall of the inflated intragastric balloon;
　positioning three or more passages extending through a side of the tubular member within the interior chamber of the inflated intragastric balloon;
　expanding an anchoring member coupled to the tubular member, the anchoring member being proximal the three or more passages and expanding radially outward from an outer surface of the tubular member, wherein the expanded anchoring member is wider than the opening in the wall of the inflated intragastric balloon; and
withdrawing the fluid by allowing the fluid to flow from the interior chamber, into the three or more passages, and into the central lumen of the tubular member.

21. A medical device, comprising:
a catheter shaft defining an outer surface, a central lumen, and a distal portion, the distal portion including a distal tip with a distal opening and three or more side passages extending through a side of the catheter shaft from the lumen to the outer surface, the distal tip being tapered,
an anchoring member coupled to the catheter shaft, the anchoring member configured to move between an unexpanded state and an expanded state, wherein the distal portion of the catheter shaft extends distal the anchoring member, wherein the three or more side passages are disposed between the distal tip and the anchoring member, and
a needle insertable through the central lumen of the catheter shaft.

* * * * *